US00PP31646P3

(12) United States Plant Patent
Hayano

(10) Patent No.: US PP31,646 P3
(45) Date of Patent: Apr. 14, 2020

(54) MINIATURE ROSE PLANT NAMED 'HOHOEMI ROUGE'

(50) Latin Name: *Rosa hybrida*
Varietal Denomination: HOHOEMI ROUGE

(71) Applicant: The Conard-Pyle Company, West Grove, PA (US)

(72) Inventor: Kimiharu Hayano, Saitama (JP)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,270

(22) Filed: Oct. 25, 2018

(65) Prior Publication Data

US 2019/0133011 P1 May 2, 2019

(30) Foreign Application Priority Data

Nov. 1, 2017 (JP) ..... PBR 32561
Sep. 24, 2018 (QZ) ..... 2018/2421

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
CPC ..... A01H 6/749; A01H 5/02
See application file for complete search history.

*Primary Examiner* — Keith O. Robinson
(74) *Attorney, Agent, or Firm* — Buchanan Ingersoll & Rooney PC

(57) ABSTRACT

A new and distinct variety of Miniature Rose Plant, herein referred to by its cultivar name, 'HOHOEMI ROUGE', is provided which forms in abundance on a nearly continuous basis attractive, small dark deep pink colored blossoms. The vegetation is vigorous and the growth habit is bushy. Attractive ornamental dark green foliage is formed. Disease tolerance to Black Spot and Rust is good. The new variety is particularly well suited for providing distinctive ornamentation in the landscape.

1 Drawing Sheet

Botanical/commercial classification:
Latin name: *Rosa hybrida.*
Common name: Miniature Rose Plant.
Varietal denomination: 'HOHOEMI ROUGE'.

CROSS-REFERNCE TO RELATED APPLICATIONS

This application claims priority to Plant Breeders' Right Application Number 2018/2421, which was filed in the European Union on Sep. 24, 2018, and to Plant Breeders' Right Application Number 32561, which was filed in Japan on Nov. 1, 2017, the contents of which are hereby expressly incorporated by reference in their entirety for all purposes.

SUMMARY OF THE INVENTION

The new variety of *Rosa hybrida* miniature rose plant of the present invention was discovered during Spring 2015 at Honjo City, Saitamam pref. Japan. The new variety is a spontaneous mutation of the 'AYA NO5' variety (not patented) and was selected and preserved primarily because of its color difference from the 'AYA NO5' parent variety.

The parentage can be summarized as follows:

spontaneous mutation of 'AYA NO5'

It was found that the new miniature rose plant of the present invention possesses the following combination of characteristics:

(a) displays a multitude of small, dark deep pink flowers,
(b) forms attractive ornamental dark green foliage, (c) forms vigorous vegetation, and
(d) exhibits good tolerance to Black Spot and Rust.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'AYA NO5' variety (i.e., the parent) exhibits light pink colored flowers, whereas the new variety displays dark deep pink colored flowers.

The new variety has been found to undergo asexual propagation in France by a number of routes including budding, grafting, and cutting. Asexual propagation in France by these routes has shown that the characteristics of the new variety are homogeneous, stable, and strictly transmissible by such asexual propagation from one generation to another. Accordingly, the new variety undergoes asexual propagation in a true-to-type manner.

The new variety has been named 'HOHOEMI ROUGE'.

BRIEF DESCRIPTION OF THE PHOTOGRAPHS

FIG. 1 provides photographs which show, as nearly true as it is reasonably possible to make the same in color illustrations of this character, typical specimens of the new variety. The illustrated rose plants of the new variety were approximately one year of age and were observed at Le Cannet des Maures, Var, France while budded on own roots and growing outdoors in July. Dimensions in centimeters are indicated at the bottom of FIG. 1. Standard color information is included at the bottom of FIG. 1. The individual elements of the photographs of FIG. 1 are described below.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—obverse.

Element 8—illustrates a specimen of a fully open flower—plan view—reverse.

Element 9—illustrates a specimen of a fully open flower—plan view—obverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 7 leaflets—plan view—upper surface.

Element 16—illustrates a specimen of buds in clusters.

Element 17—illustrates a specimen of a leaf with 3 leaflets—plan view—under surface.

Element 18—illustrates a specimen of a leaf with 5 leaflets—plan view—under surface.

Element 19—illustrates a specimen of a leaf with 7 leaflets—plan view—under surface.

DETAILED BOTANICAL DESCRIPTION

The chart used in the identification of colors is that of The Royal Horticultural Society (R.H.S. Colour Chart, edition 2001), London, England. The terminology which precedes reference to the chart has been added to indicate the corresponding color in more common terms. The description is based on the observation of one-year-old specimens of the new variety during July while budded on their own roots and growing outdoors at Le Cannet des Maures, Var, France.

Class: Miniature Rose Plant.

Plant:

*Habit*.—Bushy.

Branches:

*Color*.—Commonly near Yellow-Green Group 144B on young stems and commonly near Yellow-Green Group 146C on adult wood.

*Thorns*.—Configuration on adult stems: slightly curved downwards on the upper surface and slightly concave on the under surface. Long prickles ≥0.3 cm on young stems of about 10 cm long: quantity is commonly 8, color is commonly near Yellow-Green Group 145B, length is approximately 0.3 cm on average, and base is oval. Long prickles ≥0.3 cm on adult stems of about 10 cm long: quantity is commonly 6, color is commonly near Greyed-Orange Group 164A, length is approximately 0.4 cm on average, and base is oval. Small prickles <0.6 cm: none observed.

Foliage:

*General appearance*.—Dense with a dull aspect on both upper and under surfaces.

*Number of leaflets*.—3, 5, and 7; most often 5 or 7.

*Terminal leaflet*.—Length: approximately 1.7 cm on average. Width: approximately 0.9 cm on average.

*New foliage*.—Upper surface color: commonly near Green Group 138A. Under surface color: commonly near Green Group 138B.

*Adult foliage*.—Upper surface color: commonly near Green Group 137C. Under surface color: commonly near Green Group 138B.

Leaflets:

*Shape*.—Generally oval shaped with an cupsidate tip and an obtuse base.

*Texture*.—Upper and under surfaces are leathery.

*Edge*.—Slightly denticulate.

*Serration*.—Small and single.

*Petiole rachis*.—Color of upper surface: commonly near Green Group 138C. Color of under surface: commonly near Green Group 138B.

*Petioles*.—Upper surface texture: no glandular. Under surface texture: few prickles. Color of upper surface: commonly between near Green Group 137C and near Green Group 137D. Color of under surface: commonly near Green Group 138B. Petiole length of terminal leaflet: approximately 2.0 cm on average.

*Stipules*.—General appearance: adnate, pectinate, and narrow. Length: approximately 0.9 cm on average. Width: approximately 0.2 cm on average. Color of upper surface: commonly near Green Group 138C. Color of under surface: commonly near Green Group 138B.

Inflorescence:

*Number of flowers per stem*.—Commonly between 3 to 18 blossoms per stem.

*Buds*.—Shape: ovoid. Size: small. Length: approximately 0.6 cm on average. Width: approximately 0.6 cm on average. Color as calyx breaks, upper surface: commonly near Red Group 47B. Color as calyx breaks, under surface: commonly near Red Group 48C to Red Group 47C.

*Sepals*.—Length: approximately 0.7 cm on average. Width: approximately 0.2 cm on average. Shape: longish and narrow at the top and upright at the base; without extensions. Upper surface texture: smooth. Upper surface color: commonly near Green Group 138B. Under surface texture: smooth. Under surface color: commonly near Green Group 138B.

*Receptacle*.—Color: commonly near Green Group 138B. Length: approximately 0.3 cm on average. Width: approximately 0.2 cm on average. Surface: smooth. Shape: funnel shaped.

*Peduncle length*.—Approximately 3.4 cm on average. Width: approximately 0.2 cm on average. Surface: smooth. Color: commonly near Green Group 138B.

*Flower*.—Average open size: approximately near 2 cm on average. Shape: cup shaped. Type: semi-double. Profile of lower part of the flower: convex. Number of petals under normal conditions: commonly between 13 to 19 on average. Shape of petal: obtuse at the base and rounded at the top. Texture of the petal: upper and under surfaces are leathery. Petal length: approximately 0.7 cm on average. Petal width: approximately 0.6 cm on average. Petal arrangement: imbricated with some petaloids. Petal drop: petals drop off cleanly before drying. Fragrance: none. Color when opening on upper surface: commonly near Red Group 47D to Red Group 48A. Color when opening on under surface: commonly near Red Group 48B. Color of the open flower on upper surface: commonly near Red Group 47D to Red Group 48A. Color of the open flower on under surface: commonly near Red Group 48B to Red Group 48D. Basal spot on inner side of petal: color is commonly near Green-White Group 157D, height is typically 0.3 cm to 0.4 cm on average, width is typically 0.2 cm to 0.3 cm on average. Anthers: number is approximately 14 on average, length is approximately 0.1 cm on average, coloration is commonly near Yellow Group 8C, and arrangement is regular around styles. Filaments: length is approximately 0.1 cm on average, and coloration is commonly near Yellow Group 150D. Styles: number is approximately 4 on average, length is approximately 0.1 cm on average, and coloration is commonly near Yellow Green Group 145C. Stigmas: size is approximately 0.1 cm on average and coloration is commonly near Yellow Green Group 145C. Hip: not observed.

Development:

*Vegetation*.—Vigorous and strong.

*Blooming*.—Early in the season, very abundant and nearly continuous.

*Tolerance to diseases*.—Good, particularly against Black Spot (*Diplocarpon rosae*) and Rust (*Phragmidium mucronatum*).

Plants of the 'HOHOEMI ROUGE' variety have not been observed under all possible environmental conditions to date. Accordingly, it is possible that the phenotypic expression may vary somewhat with changes in light intensity and duration, cultural practices, and other environmental conditions.

I claim:

1. A new and distinct miniature rose plant characterized by the following combination of characteristics:

(a) displays a multitude of small, dark deep pink flowers, (b) forms attractive ornamental dark green foliage (c) forms vigorous vegetation, and (d) exhibits good tolerance to Black Spot and rust;

substantially as herein shown and described.

* * * * *

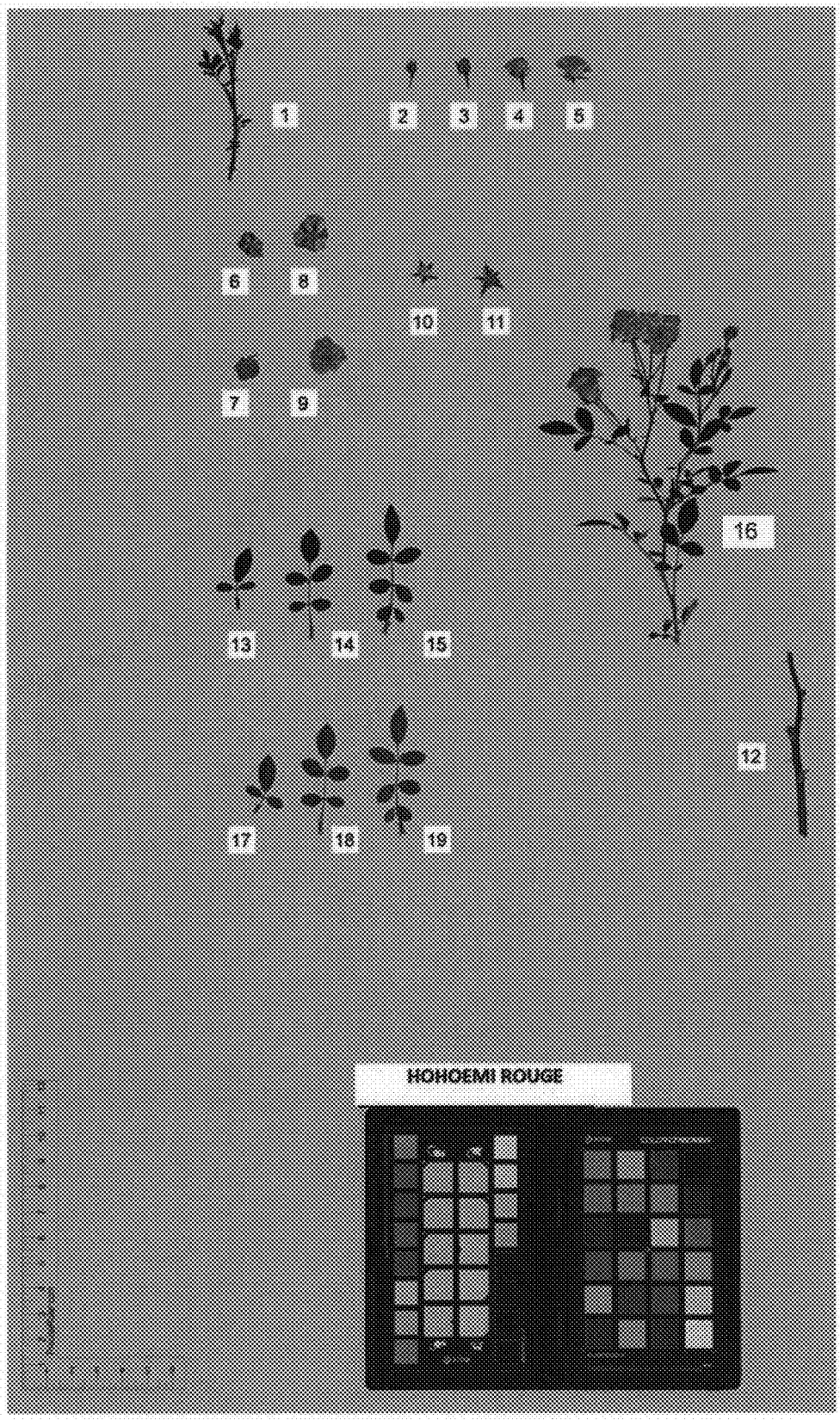
1
2
3
4
5
6
8
10
11
7
9
16
13
14
15
12
17
18
19
HOHOEMI ROUGE